(12) United States Patent
Geffard (10) Patent No.: US 7,195,881 B2
(45) Date of Patent: Mar. 27, 2007

(54) METHOD AND KIT FOR FOLLOWING NEURODEGENERATIVE DISEASES

(75) Inventor: Michel Geffard, Talence (FR)

(73) Assignee: GEMAC, Cenon Cedex (FR)

( * ) Notice: Subject to any disclaimer, the term of this patent is extended or adjusted under 35 U.S.C. 154(b) by 318 days.

(21) Appl. No.: 10/471,788

(22) PCT Filed: Mar. 15, 2002

(86) PCT No.: PCT/FR02/00927

§ 371 (c)(1),
(2), (4) Date: Sep. 16, 2003

(87) PCT Pub. No.: WO02/075274

PCT Pub. Date: Sep. 26, 2002

(65) Prior Publication Data

US 2004/0082015 A1    Apr. 29, 2004

(30) Foreign Application Priority Data

Mar. 16, 2001  (FR) ................................... 01 03592

(51) Int. Cl.
*G01N 33/53*  (2006.01)
*G01N 33/564* (2006.01)
*G01N 33/566* (2006.01)

(52) U.S. Cl. ......................... 435/7.1; 436/507; 436/513

(58) Field of Classification Search ..................... None
See application file for complete search history.

(56) References Cited

U.S. PATENT DOCUMENTS 5,047,330 A    9/1991    Grassi et al.

FOREIGN PATENT DOCUMENTS

EP            621479 A1 *  10/1994
FR          2 822 238        9/2002

OTHER PUBLICATIONS

Mark, MH. Lumping and splitting the parkinson plus syndromes. Dementia with lewy bodies, multiple system atrophy, progressive supranuclear palsy, and cortical-basal ganglionic degeneration. Neurologic Clinics, 2001, 19(3): 607-627.*
Holmberg, B. CSF-neurofilament and levodopa tests combined with discriminant analysis may contribute to the differential diagnosis of Parkinsonian syndromes. Parkinsonism & Related Disorders, 2001, 8: 23-31.*
Amara A et al. Autoantibodies to malondialdehyde-modified epitope in connective tissue disease and vasculitudes. Clin. Exp. Immunol, 1995, 101: 233-238.*
Boullerne Al et al. Circulating antibodies directed against conjugated fatty acids in sera of patients with multiple sclerosis. J. Neuroimmunol, 1996, 65: 75-81.*
Geffard M et al. Circulating antibodies directed against NO-modified self-antigens in chronic neurological and rhemumatismal diseases. Immunoanal Biol Spec, 1998, 13: 209-217 (in French, translated by The McElroy Translation Co. for the USPTO).*
Hughes Le et al. Antibody responses to *Acinetobacter* spp. and *Pseudomonas aeruginosa* in multiple sclerosis: Prospects for diagnosis using the myelin-*Acinetobacter*-neurofilament antibody index. Clin. Diag. Lab. Immunol, 2001, 8(6): 1181-1188.*
Analytical Chemistry 57 (1985) 1170-1173.
Amara A., Chaugier C. and Geffard M. Autoantibodies directed against conjugated fatty acids in sera of HIV-1 infected patients. AIDS, (1994 a) 8, 711-713.
Amara A., Chaugier C., Ragnaud J.-M. and Geffard M. Circulating autoantibodies directed against conjugated fatty acids in sera of HIV-1 infected patients. Clinical and Experimental Immunology, (1994 b) 96, 379-383.
Boullerne A., Petry K.G., Meynard M. and Geffard M. Indirect evidence for NO involvement in multiple sclerosis by characterization of circulating antibodies directed against conjugated S-nitrosocysteine. J. of Neuroimmunol., (1995) 60, 117-124.
Brochet B., Faiderbe S., Audhuy S., Gosset I., Geffard M. and Orgogozo J.M. Antibodies against phosphatidylinositol in multiple sclerosis. Current Concepts in Multiple Sclerosis—proceedings of the 6th congress of the ECTRIMS. (Wietholter M., Dichgans J.). Mertin J., Eds Excerpta Medica, Amsterdam, (1991) 97-102.
Constans J., Conri C., Pellegrin J.L., Sergeant C., Simonoff M., Peuchant E., Dubourg L., Thomas M.J., Pellegrin I., Brossard G., Barbeau P., Amara A., Geffard M., Clerc M., Fleury H. and Leng B. Stress oxydatif and infection a VIH : un concept a preciser and une voie therapeutique a explorer (<<Oxidative stress and infection with HIV : a concept to be specified and a therapeutic route to be explored>>). Annales de Medecine Interne, (1995) 146, 514-520.
Daverat P., Geffard M. and Orgogozo J.M. Identification and characterization of anti-conjugated azelaic acid antibodies in multiple sclerosis. J. of Neuroimmunology, (1989) 22, 129-134.
Faiderbe S., Chagnaud J.L., Wafflart J. and Geffard M. Autoanticorps diriges contre un phospholipide membranaire dans les serums de malades porteurs de tumeurs malignes. (<<Autoantibodies directed against a membrane phospholipid in the sera of ill subjects having malignant tumours>>). CRAS, (1990) 310, 49-52.
Maneta-Peyret L., Daverat P., Geffard M., Cassgane C. and Orgogozo J.M. Natural seric anti-fatty acid antibodies in multiple sclerosis. Neurosc. Letters, (1987) 80, 235-239.
Souan M.L. Geffard M., Lebrun-Grandie P. and Orgogozo J.M. Detection of anti-acetylcholine antibodies in myasthenic patients. Neurosc. Letters. (1986) 64, 23-28.

* cited by examiner

*Primary Examiner*—Elizabeth Kemmerer
*Assistant Examiner*—Kimberly A. Ballard
(74) *Attorney, Agent, or Firm*—Antonelli, Terry, Stout and Kraus, LLP.

(57) ABSTRACT

The invention relates to a method for detecting and supervising neurodegenerative diseases, which consists in detecting the presence of antibodies of the A-isotype and/or M-isotype which are directed against the antigens which are associated with these diseases.

The invention also relates to a kit for the implementation of this method.

27 Claims, 4 Drawing Sheets

METHOD AND KIT FOR FOLLOWING NEURODEGENERATIVE DISEASES

This application is a National Stage application under 35 USC 371 of PCT/FR02/00927, with an international filing date of Mar. 15, 2002.

A subject of the present invention is a method and a kit for the supervision of neurodegenerative diseases.

The invention can notably be applied in the medical field and in the immunological field.

Despite the immense medical progress over the last fifty years, a certain number of diseases, which are known for a long time or which are of recent appearance, remain strictly speaking incurable, despite a significant cost for Public Health. Neurodegenerative diseases may in particular be cited, such as Parkinson's disease, multiple sclerosis (MS), amyotrophic lateral sclerosis (ALS), Alzheimer's disease, auto-immune diseases, hepatites, degenerative and inflammatory rheumatisms including rheumatoid arthritis (RA).

In these diseases, the nosological diagnosis is given, certain mechanisms and stages of the lesion process are known, symptomatic treatments are given, which are often very expensive, but the results are not at the height of expectations.

Multiple sclerosis is a multilocular demyelinising pathology of the central nervous system which affects the white matter of the brain and of the spinal cord, and which is a very highly disabling pathology of insidious and unpredictable progression.

In France, MS affects 1 individual per 1000 in full maturity (40 to 60 cases for 100,000 inhabitants), i.e. 50,000 French people, and 2,000 new cases are to be counted every year. 2 million cases are counted in the world.

The disease begins in the young adult, between 15 and 50 years old (between 20 and 40 years old in particular). Its incidence is twice as much in the woman as in the man.

MS has three distinct clinical forms: remittent, progressive and remittent progressive.

Amyotrophic lateral sclerosis (ALS) or Charcot's disease is a neurological disease of rapid progression and of unknown aetiology. The disease is characterised by a degenerative attack of the motor neurones of the brain, of the cerebral trunk and of the anterior horn of the spinal cord, whereas the sensory neurones are not affected and whereas the intellectual functions remain intact, leaving the patients fully conscious of the progression of their disease and of the deterioration of their functional capacities.

The prevalence of ALS is equal to that of MS. It is five times higher than that of Huntington's disease. More ill people die every year from ALS than from MS or Huntington's disease.

ALS occurs most often between 45 and 70 years old, affecting 1.5 to 2 times more men than women. The disease concerns subjects which are younger and younger: cases exist having early beginning before 40 years old.

Its incidence, i.e. the number of new cases each year, has a tendency to increase in the world for an unknown reason. In France, there would be 5 to 10,000 persons affected, and about 1,100 new cases appear every year.

The progression of this disease is dramatic, and is always fatal. It proceeds towards a progressive aggravation, with an installation of a bedridden state and of a respiratory insufficiency through attack of the intercostal and diaphragm musculature, which rapidly leads to death (in 3 to 5 years).

ALS has a progressive clinical heterogeneity which leads a biological heterogeneity to be considered.

Rheumatoid arthritis (RA), formerly called atrophic arthritis, is a progressive chronic polyarthritic inflammatory disease which is responsible for osteocartilaginous damage, which leads to a painful functional impotence through deformation and ankylosis.

It is therefore a potentially severe disease which causes a significant handicap in over half the patients, 10 years after the beginning of the symptoms, and reduces their life expectancy by several years.

Its prevalence in France would be about 1%: it is the most frequent chronic inflammatory rheumatism. It affects 7,000 new individuals per annum, affecting more often women who are still young.

Spondylarthritis (SAR) is a chronic rheumatic disease which manifests itself by a lumbosacral attack which leads to a progressive ankylosis. This immunological and inflammatory disease is linked to an over-expression of the histocompatibility antigen B27 (found in 90% of cases).

The significance of these diseases both from the point of view of the number of persons affected, and the cost to Public Health, is therefore not negligible.

Hitherto, no biological test exists for evaluating the stage and/or for foreseeing the progression of these diseases. Only a clinical examination, optionally completed by additional examinations, enables the diagnosis of these diseases to be made. A real need therefore does exist to be able to have a specific progressive diagnostic test at one's disposal which can palliate the insufficiencies of the clinic.

The Applicant has demonstrated that the occurrence of neurodegenerative diseases was associated with antigen modifications, which are integrated by immunocompetent cells, manifesting itself by the production of circulating antibodies of the A-isotype and/or M-isotype. These antibodies are directed against the antigens indicated in Table 1 below, showing the antigen modifications and the bacterial factors which participate in the chronicity of these diseases:

TABLE 1

| Antigens | Origin | Isotype of the antibody |
|---|---|---|
| Fatty acids (palmitic, oleic, myristic acids) Farnesyl Cysteine | Endogenous compounds linked by amide bond | M |

TABLE 1-continued

| Antigens | Origin | Isotype of the antibody |
|---|---|---|
| Phosphatidylinositol | | |
| Acetylcholine | | |
| Azelaic acid | Modified endogenous compound (amide bond) | M |
| Malondialdehyde residue | product very reactive with endogenous constituents | M |
| NO-Cysteine | Endogenous constituents modified by ·NO and ROE (reactive oxygen species) | M |
| NO-Tyrosine | | |
| NO-Tryptophan | | |
| NO-Histidine | | |
| NO2-Tyrosine | | |
| NO-Phenylalanine | | |
| NO-Arginine | | |
| NO-Asparagine | | |
| NO-Methionine | | |
| NO-Creatine | | |
| NO-Bovine Serum Albumin | | |
| bacterial antigens 3 (Ig3) | *Hafnia alvei* | A or M |
| bacterial antigens 5 (Ig5) | *Pseudomonas aeruginosa* | A or M |
| bacterial antigens 12 (Ig12) | *Morganella morganii* | A or M |
| bacterial antigens 13 (Ig13) | *Proteus mirabilis* | A or M |
| bacterial antigens 16 (Ig16) | *Pseudomonas putida* | A or M |
| bacterial antigens 17 (Ig17) | *Citrobacter diversus* | A or M |
| bacterial antigens 19 (Ig19) | *Klebsiella pneumoniae* | A or M |

The detection of these antibodies can therefore enter within the context of a general diagnosis of neurodegenerative diseases, and the supervision of these diseases.

Such a method of detecting these antibodies in a biological fluid can comprise the following steps:

placing said fluid in contact with each one of the following antigens: Pal, Ole, Myr, Pl, MDA, Ach, FarCys, Aze, NO-Cys, NO-Tyr, NO-Trp, NO-His, NO2-Tyr, NO-Phe, NO-Arg, NO-Asn, NO-Met, NO-Cr, NO-BSA, Ig3, Ig5, Ig12, Ig13, Ig16, Ig17, Ig19 and revelation of the complexes which are optionally formed between said antigens and the corresponding antibodies.

As is indicated in Table 1, when the presence is detected of an antibody directed against a bacterial antigen "Ig", this antibody can be of the A-isotype and/or of the M-isotype.

Non-bacterial antigens other than bovine serum albumin, which is optionally nitrosylated, are advantageously conjugated.

The term "conjugated antigen" is understood in the sense of the present invention to be an antigen (such as Pal, FarCys, NO-Cys, etc.) which is coupled to a carrier molecule, preferably bovine serum albumin, either directly or via glutaraldehyde or glutaric anhydride. Such a coupling is made in a manner well-known to the person skilled in the art, e.g. as described in Boullerne et al., 1995, 1996; Geffard et al., 1998.

The bacterial antigens are obtained by sonication of cultures of the bacteria indicated in Table 1.

The biological fluid can be, in particular: a serum, a plasma, total blood, urine, cerebrospinal fluid.

The method implemented can advantageously be of the "sandwich" type.

The complexes which are optionally formed can be revealed with the aid of an A or M anti-human immunoglobulin antibody, which is coupled to a label, e.g. a fluorescent label, the biotin/streptavidine system, a (radio)isotopic element, or an enzyme.

The method in accordance with the invention is advantageously carried out with the aid of a suitable solid support.

Any device can be used as a solid support which is adapted to the manipulation of cell suspensions and, preferably, tubes, particular magnetic supports or rigid or flexible microtitration plates of polyethylene, polystyrene, poly (vinyl chloride) or nitrocellulose, comprising microwells.

When a pre-activated microtitration plate is used which has NH2 termini, it is not necessary to "couple" the antigens to a carrier molecule.

The expression "an antibody coupled to a (radio)isotopic element" signifies that the antibody carries, either on an element proper of its structure, e.g. the constituent tyrosine residues, or on an appropriate radical which has been fixed to it, a radioactive isotope enabling it to be determined by counting of the radioactivity which is associated with it.

When the antibody is coupled to an enzyme, this, associated with the use of appropriate reagents, enables a quantitative measurement of this antibody.

The substrate and the reagents are selected so that the final product of the reaction or of the sequence of reactions caused by the enzyme and using these substances be:

a coloured or fluorescent substance which diffuses into the liquid medium surrounding the cells and which is the subject of the final spectrophotometric or fluorimetric measurement, respectively, or an insoluble coloured substance which is deposited on the cells and the walls on which they are fixed and which can be the subject, either of a photometric measurement by reflection, or of a visual evaluation, optionally in comparison to a range of standard tints.

When a radio-isotopic element is used, such as 125 iodine for example, the radioactivity associated with the sample is counted in a gamma counter according to any appropriate means.

When an enzyme is used, the appearance of a coloured or fluorescent product is obtained by adding to the solid support a solution which contains the substrate of the enzyme and one or more additional reagents enabling either a coloured product which is soluble in the medium, or an insoluble coloured product, or a soluble fluorescent product, as has been explained above, to be finally obtained. The light signal originating from the thus-treated samples is then measured with the aid of an apparatus which is adapted to each case: a transmission or reflection photometer, or fluorimeter, respectively. When the solid support is a microtitration plate, the reading of the light signal can be made sequentially in all the wells of the same plate by the use of usual automated readers which are common in biology laboratories.

Alkaline phosphatase can be used as enzyme, the preferential substrates of which are para-nitrophenylphosphate for a final spectrophotometric reading, or 4-methyl umbelliferylphosphate for a fluorimetric reading, or 5-bromo-4-chloro-3-indolylphosphate for obtaining an insoluble coloured reaction product. β-galactosidase can similarly be used as enzyme the preferential substrate of which is ortho-nitrophenyl-β-D-galactopyranoside.

Preferably, the anti-Ig antibodies can be conventionally coupled to peroxidase. The reagents used to reveal the peroxidase conjugated to the anti-Ig antibodies contains hydrogen peroxide, which is a substrate of the enzyme, and an appropriate chromogen, e.g. ortho-phenylenediamine, 3,3'-diaminobenzidine or TMB (3,3',5,5'-tetramethylbenzidine) in order to obtain an insoluble final reaction product, or even para-hydroxyphenylpropionic acid in order to obtain a fluorescent reaction product which is soluble in the medium. The colourimetric reaction is stopped with sulphuric acid.

Another preferred embodiment of the invention is the use of anti-immunoglobulin antibodies which are coupled to acetylcholinesterase.

Acetylcholinesterase is coupled to the antibody by preferably using a method which is derived from the one described in French patent No. 2,550,799, or a method which schematically comprises the preparation of fragments of the antibody by a known technique, the modification of the enzyme by reaction with an appropriate heterobifunctional agent, and, finally, the coupling of the products thus obtained.

The revelation of the enzyme activity is preferably made according to the well-known technique which makes use of acetylthiocholine as substrate of the enzyme and Ellman's reagent, or 5,5'-dithio-2-nitrobenzoic acid, as chromogen, according to any variant adapted to the case examined, e.g. the one described in Anal. Chem. 57 (1985) 1170–1173.

The chromogens cited are used as such or as water-soluble salts.

Another subject of the invention is a kit for the implementation of the method described above. This kit advantageously comprises:
  each one of the following antigens: Pal, Ole, Myr, Pl, MDA, Ach, FarCys, Aze, NO-Cys, NO-Tyr, NO-Trp, NO-His, NO2-Tyr, NO-Phe, NO-Arg, NO-Asn, NO-Met, NO-Cr, NO-BSA, Ig3, Ig5, Ig12, Ig13, Ig16, Ig17 and Ig19;
  optionally at least one human anti-immunoglobulin antibody, of the A-isotype and/or M-isotype, as defined above.

The detection of the antibodies directed against the following antigens: Pal, Ole, Myr, Pl, MDA, FarCys, Aze, NO-Cys, NO-Phe, Ig3 (A-isotype antibody and M-isotype antibody), Ig5 (A-isotype antibody and M-isotype antibody), Ig12 (A-isotype antibody and M-isotype antibody), Ig13 (M-isotype antibody) and Ig19 (A-isotype antibody), enables the diagnosis of RA to be established.

In the description and the claims, the following abbreviations will be used:
  BSA: bovine serum albumin
  G: glutaraldehyde residue
  GA: glutaric anhydride residue
  PBS: phosphate buffer saline
  OPD: ortho-phenylenediamine
  H2O2: hydrogen peroxide
  H2SO4: sulphuric acid
  PI: phosphatidylinositol
  CaCl2: calcium chloride
  NaCl: sodium chloride
  OD: optical density
  HSA: human serum albumin
  HSA-EA: human serum albumin on which ethylenediamine is attached
  Ig: immunoglobulin
  Ach: acetyl choline
  Ole: oleic acid
  Pal: palmitic acid
  Myr: myristic acid
  FarCys: Farnesyl cysteine

This kit can also comprise a suitable solid support.

This test notably enables:
  establishing an early diagnosis of the disease, in particular in persons at risk, and therefore to not create a delay in the treatment of the disease;
  supervising the progress of the disease, and therefore to be able to adapt the treatment as a consequence.

The detection of the antibodies directed against the following antigens: PI, Ach, Aze, NO-Cys, NO-Tyr, NO-Trp, NO2-Tyr, NO-Asn, NO-Met, Ig5 (A-isotype antibody), Ig12 (A-isotype antibody and M-isotype antibody), Ig13 (A-isotype antibody), Ig16 (A-isotype antibody), Ig17 (M-isotype antibody) and Ig19 (A-isotype antibody), enables in particular the diagnosis of MS to be established. The quantification of the antibodies directed against the following antigens: NO2-Tyr, NO-Tyr, Ach and Ig16 (A-isotype antibody), enables discriminating the particular forms of MS (progressive, remittent, remittent progressive).

Similarly, the detection of the antibodies which are directed against the following antigens: Ole, Pl, MDA, Aze, NO-Cys, FarCys, Ig3 (A-isotype antibody and M-isotype antibody), Ig5 (A-isotype antibody), Ig12 (A-isotype antibody and M-isotype antibody), Ig13 (A-isotype antibody and M-isotype antibody), Ig16 (A-isotype antibody and M-isotype antibody), Ig17 (A-isotype antibody and M-isotype antibody), enables the diagnosis of ALS to be established and, as a function of the antibody titre, to differentiate the 3 classes of this disease.

MDA: malondialdehyde
(neo-epitope resulting from lipoperoxidation)

(with R=protein)
NO-Cys: NO-cysteine
(neo-epitope due to nitrosylation of cysteine)

NO-Trp: NO-tryptophan
(neoepitope due to nitrosylation of tryptophan)

NO-Asn: NO-asparagine
(neoepitope due to nitrosylation of asparagine)

NO-Tyr: NO-tyrosine
(neoepitope due to nitrosylation of tyrosine)

NO2-Tyr: NO2-tyrosine
(neoepitope due to formation of peroxynitrite: NO+O2-)

NO-His: NO-histidine
(neoepitope due to nitrosylation of histidine)

NO-Phe: NO-phenylalanine
(neoepitope due to nitrosylation of phenylalanine)

NO-Met: NO-methionine
(neoepitope due to nitrosylation of methionine)

NO-Arg: NO-arginine
(neoepitope due to nitrosylation of arginine)

NO-Cr: NO-creatine
(neoepitope due to nitrosylation of creatine)

The invention will be better understood with the aid of the Sections and Examples below, which are given purely as an illustration.

Section 1: Assay of Anti-No-Cysteine Antibodies

A Maxisorp® microtitration plate comprising 96 wells is used which is marketed by the company MERCK-EUROLAB (POLYLABO). 10 µg/ml of a solution of NO-Cysteine-G-BSA conjugate (prepared according to the method described in Boullerne et al., 1995, 1996 and Geffard et al., 1998), in pH 9.6 carbonate buffer (reaction blanks: BSA-G), is placed per well for one night at +4° C. under stirring, in avoiding the exposure of the plate to the light. PBS buffer containing Tween®, 10% glycerol and 1 g/l of BSA is then added into the wells, so as to saturate the surface of the wells with protein, which is obtained after 1 h at 37° C. Rinsing is effected thrice with PBS.

The serum to be assayed, which is diluted to a 1/1000th in PBS buffer containing Tween®, 10% glycerol and 1 g/l of BSA-G, is then added, and incubation is implemented for 2 hours at 37° C.

A solution to a 1/5,000th of human anti-IgM antibodies (marketed by Sanofi Pasteur under the reference 75061), which are labelled with peroxidase, in PBS buffer containing Tween® and 1 g/l of BSA, is then added into the wells, and incubation is implemented for 1 hour at 37° C. The plate is rinsed thrice with PBS containing Tween®.

The wells are emptied by turning the plate over. Revelation reagent is added into each well (for 20 ml of citrate phosphate buffer, 10 µl of $H_2O_2$ (substrate of the enzyme) and 0.5 ml of 4% OPD are added) and the colouration is allowed to take place in the dark for 10 minutes. The reaction is stopped with 50 µl of 4N $H_2SO_4$, and the OD is read at 492 nm.

The results are then expressed with respect to a population of controls in the following way:

Antibody titre=(OD serum−ODav. controls)/ODav. controls.

Section 2: Assay of Anti-Phosphatidylinositol Antibodies

A Maxisorp® microtitration plate is used. 20 µg/ml of a coating solution is added per well (Faiderbe et al., 1990; Brochet et al., 1991), which solution is prepared from 20 ml of $10^{-2}$M phosphate buffer+$10^{-3}$M $CaCl_2$, pH 7, and which is saturated with chloroform, to which are added 40 µl of the mother solution of phosphatidylinositol (marketed by SIGMA, reference P-5766), with a Hamilton syringe, and 100 µl of a hexane/chloroform (84/16) mixture, in order to allow the PI to pass into solution (reaction blanks: BSA). The wells are vortexed until a white precipitate is obtained. The plate is then left for one night at 37° C. under stirring. The plate is dried in the oven for at least 30 minutes, and rinsing is effected thrice with PBS.

The serum to be assayed is then added, which is obtained in the following manner: the night before the assay, a pre-dilution of the serum (1/10th) is prepared in PBS buffer containing 27 g/l of NaCl, and stirring is effected at 4° C. overnight. Centrifugation is implemented for 15 minutes at 10,000 rpm. From the supernatant, dilution is made to a 1/50th (final dilution to a 1/500th in PBS buffer containing 10% of glycerol and 1 g/l of HSA-EA).

A solution to a ⅕,₀₀₀th of human anti-IgM antibodies (SANOFI-PASTEUR, reference 75061), which are labelled with peroxidase, in PBS buffer containing Tween® and 1 g/l of BSA, is finally added to the wells, and incubation is implemented for 2 hours at 37° C. The plate is rinsed thrice with PBS containing Tween®.

The wells are emptied by turning the plate over. Revelation reagent is added into each well (for 20 ml of citrate phosphate buffer, 20 µl of $H_2O_2$ and 1 ml of 4% OPD, are added) and the colouration is allowed to take place in the dark for 10 minutes. The reaction is stopped with 50 µl of 4N $H_2SO_4$, and the OD is read at 492 nm.

The results are then expressed with respect to a population of controls in the following way:

Antibody titre=(OD serum−ODav. controls)/ODav. controls.

Section 3: Assay of Anti-Acetylcholine Antibodies

A Maxisorp microtitration plate is used. 10 µg/ml of a solution of choline-GA-BSA conjugate (prepared according to the method described in Souan et al., 1986), in pH 9.6 carbonate buffer (reaction blanks: BSA), is placed per well for one night at +4° C. under stirring. PBS buffer containing Tween®, 10% glycerol and 1 g/l of BSA-GA is then added into the wells, so as to saturate the surface of the wells with protein, which is obtained after 1 h at 37° C. Rinsing is effected thrice with PBS.

The serum to be assayed, which is diluted to a ¹⁄₁,₀₀₀th in PBS buffer containing Tween® and 1 g/l of BSA-GA, is then added, and incubation is implemented for 2 hours at 37° C. The plate is rinsed thrice with PBS containing Tween®.

A solution to a ¹⁄₁₀,₀₀₀th of human anti-IgM antibodies (SANOFI-PASTEUR, reference 75061), which are labelled with peroxidase, in PBS buffer containing Tween® and 1 g/l of BSA, is finally added into the wells, and incubation is implemented for 1 hour at 37° C. The plate is rinsed thrice with PBS containing Tween®.

The wells are emptied by turning the plate over. Revelation reagent is added into each well (for 20 ml of citrate phosphate buffer, 10 µl of $H_2O_2$ and 0.5 ml of 4% OPD are added) and the colouration is allowed to take place in the dark for 10 minutes. The reaction is stopped with 50 µl of 4N $H_2SO_4$, and the OD is read at 492 nm.

The results are then expressed with respect to a population of controls in the following way:

Antibody titre=(OD serum−ODav. controls)/ODav. controls.

Section 4: Assay of Anti-Azelaic Acid Antibodies

A Maxisorp microtitration plate is used. 10 µg/ml of a solution of Aze-BSA conjugate (prepared according to the method described in Daverat et al., 1989), in pH 9.6 carbonate buffer (reaction blanks: BSA), is placed per well for one night at +4° C. under stirring. PBS buffer containing Tween®, 10% glycerol and 1 g/l of HSA-EA, is then added into the wells, so as to saturate the surface of the wells with protein, which is obtained after 1 h at 37° C. Rinsing is effected thrice with PBS.

The serum to be assayed, which is diluted to a ¹⁄₅₀₀th in PBS buffer containing Tween®, 10% glycerol and 1 g/l of HSA-EA, is then added and incubation is implemented for 2 hours at 37° C. The plate is rinsed thrice with PBS containing Tween®.

A solution to a ¹⁄₁₀,₀₀₀th of human anti-IgM antibodies (SANOFI-PASTEUR, reference 75061), which are labelled with peroxidase, in PBS buffer containing Tween® and 1 g/l of BSA, is finally added into the wells, and incubation is implemented for 1 hour at 37° C. The plate is rinsed thrice with PBS containing Tween®.

The wells are emptied by turning the plate over. Revelation reagent is added into each well (for 20 ml of citrate phosphate buffer, 10 µl of $H_2O_2$ and 0.5 ml of 4% OPD are added) and the colouration is allowed to take place in the dark for 10 minutes. The reaction is stopped with 50 µl of 4N $H_2SO_4$, and the OD is read at 492 nm.

The results are then expressed with respect to a population of controls in the following way:

Antibody titre=(OD serum−ODav. controls)/ODav. controls.

Section 5: Assay of Anti-Farnesol-Cysteine Antibodies

A Maxisorp® microtitration plate is used. 20 µg/ml of a solution of FarCys-BSA conjugate (prepared by activation of FarCys with ethyl chloroformate and then coupling with BSA according to the technique indicated for the fatty acids in Section 7, below) in pH 9.6 carbonate buffer (reaction blanks: BSA), are placed per well for one night at +4° C. under stirring. Rinsing is effected thrice with PBS. PBS buffer containing 27 g/l of NaCl and 2 g/l of de-lipidised BSA is then added into the wells, so as to saturate the surface of the wells with protein, which is obtained after 1 h at 37° C. Rinsing is effected thrice with PBS.

The serum to be assayed, which is diluted to a ¹⁄₂₅₀th in PBS buffer containing 27 g/l of NaCl and 2 g/l of de-lipidised BSA, is then added, and incubation is implemented for 2 hours at 37° C. Rinsing is effected thrice with PBS. A solution to a ⅕,₀₀₀th of human anti-IgM antibodies (SANOFI-PASTEUR, reference 75061), which are labelled with peroxidase, in PBS buffer containing Tween® and 1 g/l of BSA, is finally added to the wells, and incubation is implemented for 1 hour at 37° C. The plate is rinsed thrice with PBS containing Tween®.

The wells are emptied by turning the plate over. Revelation reagent is added into each well (for 20 ml of citrate phosphate buffer, 20 µl of $H_2O_2$ and 1 ml of 4% OPD, are added) and the colouration is allowed to take place in the dark for 10 minutes. The reaction is stopped with 50 µl of 4N $H_2SO_4$, and the OD is read at 492 nm.

The results are then expressed with respect to a population of controls in the following way:

Antibody titre=(OD serum−ODav. controls)/ODav. controls.

Section 6: Assay of Anti-MDA Antibodies

A Maxisorp® microtitration plate is used. 80 µg/ml of a solution of MDA-BSA conjugate (prepared according to the method described in Amara et al., 1995) in pH 9.6 carbonate buffer (reaction blanks: BSA), is placed per well for one night at +4° C. under stirring. PBS buffer containing Tween®, 10% glycerol and 5 g/l of BSA is then added into the wells so as to saturate the surface of the wells with protein, which is obtained after 1 h at 37° C. Rinsing is effected thrice with PBS. The serum to be assayed, which is diluted to a ¹⁄₁,₀₀₀th in PBS buffer containing Tween® and 5 g/l of BSA, is then added, and incubation is implemented for 2 hours at 37° C. Rinsing is effected thrice with PBS.

A solution to a ⅕,₀₀₀th of human anti-IgM antibodies (SANOFI-PASTEUR, reference 75061), which are labelled with peroxidase, in PBS buffer containing Tween® and 5 g/l of BSA, is finally added into the wells and incubation is implemented for 1 hour at 37° C. The plate is rinsed thrice with PBS containing Tween®.

The wells are emptied by turning the plate over. Revelation reagent is added into each well (for 20 ml of citrate phosphate buffer, 10 µl of $H_2O_2$ and 0.5 ml of 4% OPD, are added) and the colouration is allowed to take place in the dark for 10 minutes. The reaction is stopped with 50 µl of 4N $H_2SO_4$, and the OD is read at 492 nm.

The results are then expressed with respect to a population of controls in the following way:

Antibody titre=(OD serum−ODav. controls)/ODav. controls.

Section 7: Assay of Anti-Fatty Acids Antibodies

A Maxisorp® microtitration plate is used. 50 µg/ml of a solution of Ole-BSA, Pal-BSA or Myr-BSA conjugate (which are prepared according to the method described in Maneta et al., 1987; Amara et al., 1994 a and b, Constans et al., 1995; Boullerne et al., 1996) in carbonate buffer containing $10^{-3}$M $CaCl_2$, pH 9.6 (reaction blanks: de-lipidised BSA), is placed per well for one night at +4° C. under stirring. Rinsing is effected thrice with PBS containing $10^{-3}$M $CaCl_2$.

The serum to be assayed, which is diluted to a 1/1000th in PBS buffer containing $10^{-3}$M $CaCl_2$ and 1 g/l of de-lipidised BSA, is then added, and incubation is implemented for 2 hours at 37° C. Rinsing is effected thrice with PBS containing $10^{-3}$M $CaCl_2$.

A solution to a 1/5,000th of human anti-IgM antibodies (SANOFI-PASTEUR, reference 75061), which are labelled with peroxidase, in SPB buffer containing $10^{-3}$M $CaCl_2$ and 1 g/l of de-lipidised BSA, is finally added to the wells, and incubation is implemented for 1 hour at 37° C. The plate is rinsed thrice with SPB containing Tween®.

The wells are emptied by turning the plate over. Revelation reagent is added into each well (for 20 ml of citrate phosphate buffer, 10 µl of $H_2O_2$ and 0.5 ml of 4% OPD, are added) and the colouration is allowed to take place in the dark for 10 minutes. The reaction is stopped with 50 µl of 4N $H_2SO_4$, and the OD is read at 492 nm.

The results are then expressed with respect to a population of controls in the following way:

Antibody titre=(OD serum−ODav. controls)/ ODav. controls.

Section 8: Assay of Anti-Bacterial Antigen Antibodies

A Maxisorp® microtitration plate is used. 34 µg/ml of bacterial antigen lysate, obtained by sonication of a culture of the corresponding bacterium (cf. Table 1), in pH 9.6 carbonate buffer (reaction blanks: BSA), is placed per well for one night at +4° C. under stirring. PBS buffer containing 5 g/l of BSA is then added into the wells, so as to saturate the surface of the wells with protein, which is obtained after 1 h at 37° C. Rinsing is effected thrice with PBS containing Tween®.

The serum to be assayed, which is diluted to a 1/500th in PBS buffer containing Tween® and 2.5 g/l of BSA, is then added, and incubation is implemented for 2 hours at 37° C. Rinsing is effected thrice with PBS containing Tween®.

A solution to a 1/5,000th of human anti-IgA or anti-IgM antibodies (SANOFI-PASTEUR, references 75041 and 75061), which are labelled with peroxidase, in PBS buffer containing Tween® and 2.5 g/l of BSA, is finally added into the wells, and incubation is implemented for 1 hour at 37° C. The plate is rinsed thrice with PBS containing Tween®.

The wells are emptied by turning the plate over. Revelation reagent is added into each well (for 20 ml of citrate phosphate buffer, 10 µl of $H_2O_2$ and 0.5 ml of 4% OPD, are added) and the colouration is allowed to take place in the dark for 10 minutes. The reaction is stopped with 50 µl of 4N $H_2SO_4$, and the OD is read at 492 nm.

The results are then expressed with respect to a population of controls in the following way:

Antibody titre=(OD serum−ODav. controls)/ODav. controls.

EXAMPLE 1

Quantification of Circulating Antibodies in MS

Table 1 below groups the results of the immunoenzymatic tests carried out on a large number of subjects according to the method described in the preceding sections.

TABLE 1

| conjugate | n: MS/control | p |
|---|---|---|
| Pal | 755/238 | 0.0095 |
| Myr | 730/234 | 0.0302 |
| Ole | 1399/226 | 0.0115 |
| FarCys | 718/235 | <0.0001 |
| Aze | 1459/232 | <0.0001 |
| NOCys | 1314/234 | <0.0001 |
| NOTyr | 279/135 | <0.0001 |
| NO2Tyr | 251/126 | 0.0067 |
| NOTrp | 288/148 | <0.0001 |
| NOMet | 218/101 | 0.0022 |
| NOHis | 266/147 | <0.0001 |
| NOPhe | 243/116 | <0.0001 |
| NOAsn | 180/101 | 0.0092 |
| NOArg | 177/81 | 0.0033 |
| NOBSA | 264/135 | 0.6784 |
| NOCr | 108/46 | 0.0718 |
| MDA | 670/206 | <0.0001 |
| Ach | 731/229 | 0.0001 |
| PI | 1387/209 | <0.0001 |
| Ig3* | 658/219 | <0.0001 |
| Ig5* | 670/222 | 0.0010 |
| Ig16* | 670/218 | 0.0040 |
| Ig12* | 670/221 | 0.0524 |
| Ig13* | 670/221 | 0.2023 |
| Ig17* | 670/222 | 0.9243 |
| Ig19* | 299/95 | 0.9785 |
| Ig3** | 657/226 | <0.0001 |
| Ig5** | 669/222 | 0.0009 |
| Ig16** | 669/225 | 0.0909 |
| Ig12** | 669/223 | 0.9913 |
| Ig13** | 669/220 | 0.1731 |
| Ig17** | 668/222 | 0.0133 |
| Ig19** | 299/97 | 0.7493 |

*M-isotype antibody
**A-isotype antibody

A statistically significant antibody response was found in favour of MS for 23 conjugates out of 33.

As an example, the specificity of the anti-NO-Cys response vis-à-vis the MS was compared with that of the control neurodegenerative diseases in which radical processes were found to be involved: amyotrophic lateral sclerosis, epilepsies and Parkinson's disease. The results showed a significant difference in this response between the various pathologies in favour of MS.

Table 2 below shows the relationship between the various forms of MS (P: progressive; R: remittent; RP: remittent progressive; CON: controls) from 16 significant conjugates.

TABLE 2

| conjugate | n: MS P/CON | p1 | n: MS R/CON | p1 | n: MS RP/CON | p1 | n: MS P/R/RP | p2 |
|---|---|---|---|---|---|---|---|---|
| Aze | 259/232 | 0.0032 | 164/232 | 0.0046 | 111/232 | 0.4149 | 259/164/111 | 0.0343 |
| NOCys | 240/234 | 0.0078 | 152/234 | <0.0001 | 111/234 | 0.0073 | 240/152/111 | 0.0046 |
| NOTyr | 36/135 | 0.0762 | 53/135 | <0.0001 | 40/135 | <0.0001 | 36/53/40 | 0.0494 |
| NO2Tyr | 39/126 | 0.3829 | 59/126 | 0.0096 | 40/126 | 0.0311 | 39/59/40 | 0.0409 |
| NOTrp | 38/148 | 0.5177 | 54/148 | <0.0001 | 39/148 | 0.0899 | 38/54/39 | 0.0006 |
| NOMet | 36/101 | 0.8718 | 49/101 | 0.0005 | 39/101 | 0.9574 | 36/49/39 | 0.0393 |
| NOAsn | 25/101 | 0.5167 | 49/101 | 0.0065 | 34/101 | 0.6982 | 25/49/34 | 0.0380 |
| Ach | 117/229 | 0.5938 | 112/229 | <0.0001 | 71/229 | 0.1375 | 117/112/71 | <0.0001 |
| PI | 253/209 | <0.0001 | 161/209 | <0.0001 | 109/209 | 0.1040 | 253/161/109 | 0.0117 |
| Ig12* | 110/221 | 0.1162 | 107/221 | 0.0412 | 68/221 | 0.4858 | 110/107/68 | 0.0290 |
| Ig17* | 110/222 | 0.0002 | 107/222 | 0.4582 | 68/222 | 0.2827 | 110/107/68 | 0.0123 |
| Ig5** | 109/222 | 0.0549 | 107/222 | 0.9743 | 68/222 | 0.0016 | 109/107/68 | 0.0406 |
| Ig16** | 109/225 | 0.2218 | 107/225 | 0.0067 | 68/225 | 0.2997 | 109/107/68 | 0.0491 |
| Ig12** | 109/223 | 0.1433 | 107/223 | 0.0312 | 68/223 | 0.2231 | 109/107/68 | 0.0185 |
| Ig13** | 109/220 | 0.6407 | 107/220 | 0.0001 | 68/220 | 0.1543 | 109/107/68 | 0.0124 |
| Ig19** | 50/97 | 0.2028 | 73/97 | 0.0173 | 42/97 | 0.8779 | 50/73/42 | 0.0151 |

Figure 1:
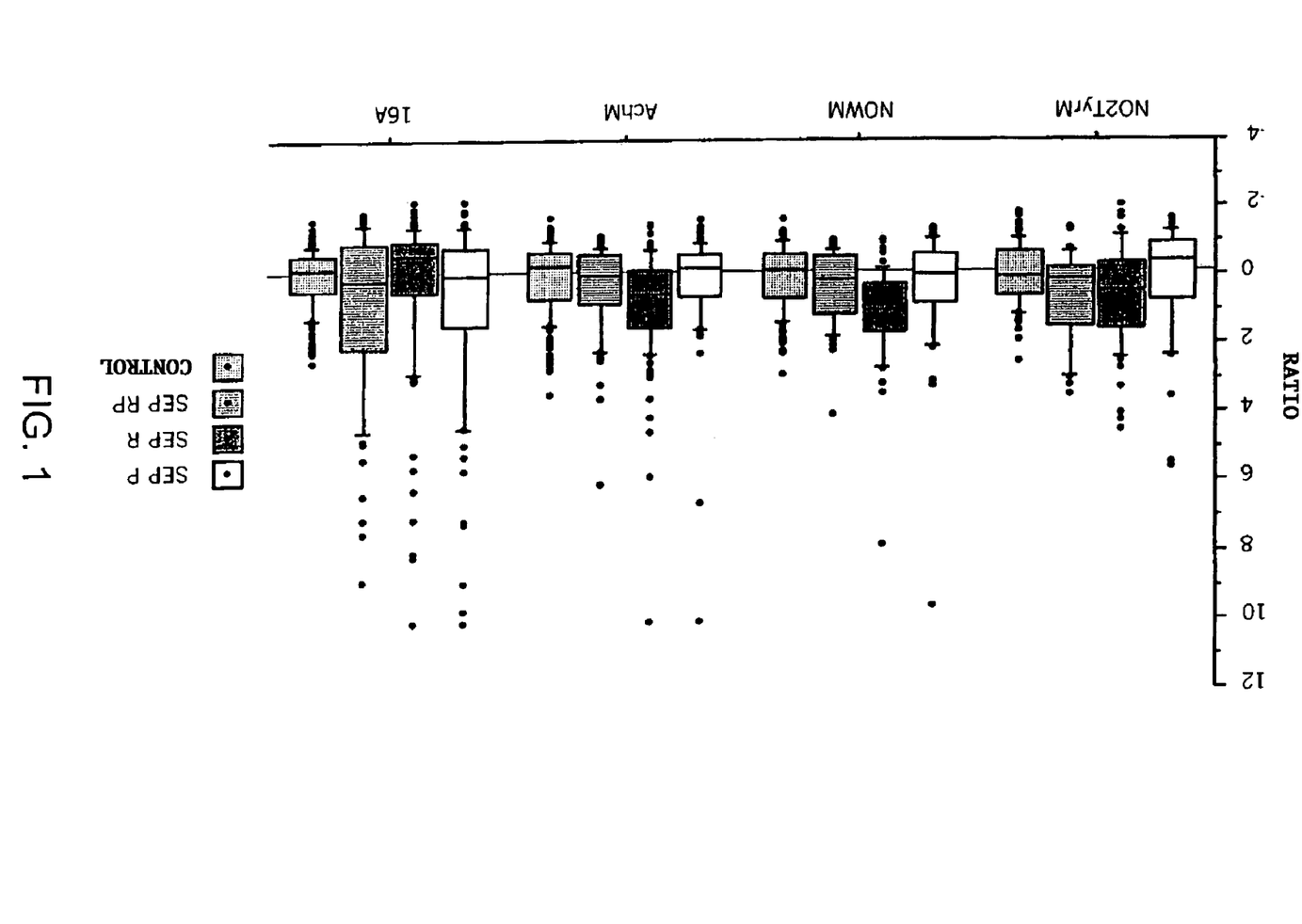
FIG. 1 is a box-plot representation of the results obtained from the quantification of immune complexes detected with 4 antigens tested according to the invention (NO2Tyr, NO-Trp, Ach and lg16) in the serum from patients having each form of MS (i.e. progressive form (P), remittent form (R) and remittent progressive form (RP) compared with that of controls). In such a graphic representation, the ratio conventionally corresponds to: (OD of a patient–average OD of controls)/standard deviation from OD of controls.

1 Mann-Whitney test
2 Kruskal-Wallis test
*M-isotype antibody
**A-isotype antibody FIG. 1 shows the distribution of the data for each form of MS and the controls.

| Antigen | NO2Tyr | NOTrp | Ach | Ig16 1 |
|---|---|---|---|---|
| p 2 | 0.0409 | 0.0006 | <0.0001 | 0.0491 |
| n MS P | 39 | 38 | 117 | 109 |
| n MS R | 59 | 54 | 112 | 107 |
| n MS RP | 40 | 39 | 71 | 68 |
| n Control | 126 | 148 | 229 | 225 |

(1 A-isotype antibody; 2 Kruskal-Wallis test)

Each conjugate discriminates, in a particular manner, the clinical forms of MS:

The anti-NO2-Tyr antibodies are particularly pertinent for discriminating the progressive and remittent-progressive forms (Mann-Whitney p between these two samples=0.0167).

The low values for the progressive MSs are noted.

The anti-NO-Trp antibodies are good indicators for discriminating the progressive and remittent forms (Mann-Whitney p<0.0001).

The anti-Ach antibodies are pertinent for discriminating the remittent form from the two other forms (Mann-Whitney p<0.0001).

The anti-A-isotype Ig16 antibodies are pertinent for discriminating the progressive and remittent forms (Mann-Whitney p<0.01).

These circulating antibodies enable the forms of MS and above all the passage of one progressive form to another (remittent form/progressive form) to be discriminated. It is not possible to identify this progression by any other current clinical or exploratory approach.

EXAMPLE 2

Quantification of Circulating Antibodies in ALS

Figure 2:
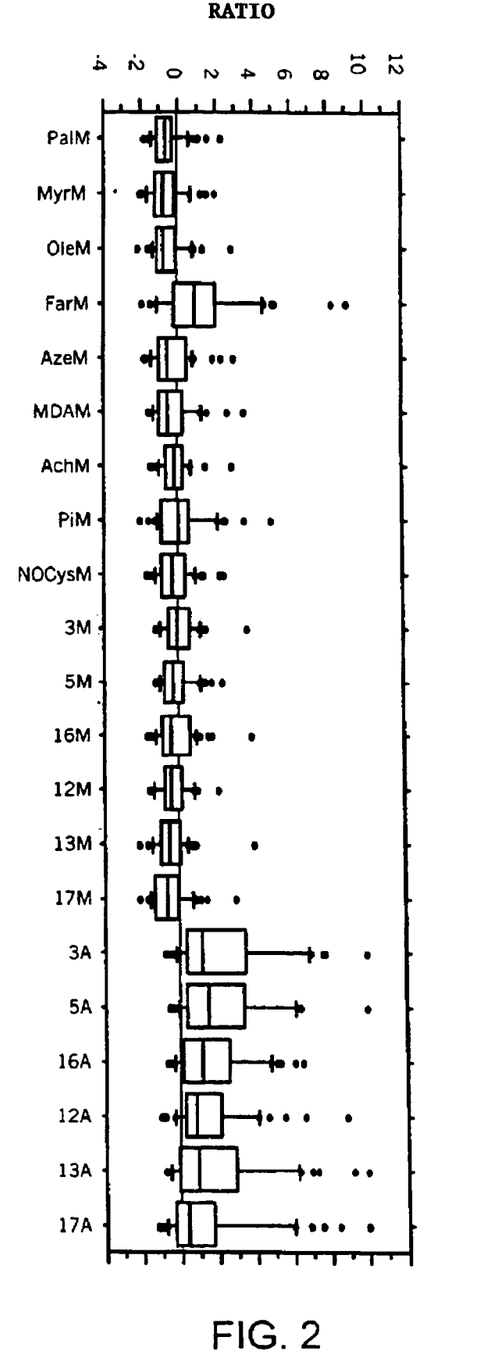
FIG. 2 is a box-plot representation of the results obtained from the quantification of immune complexes detected with 21 antigens tested in the serum from patients having class 1 of ALS compared with that of controls.
Figure 3:
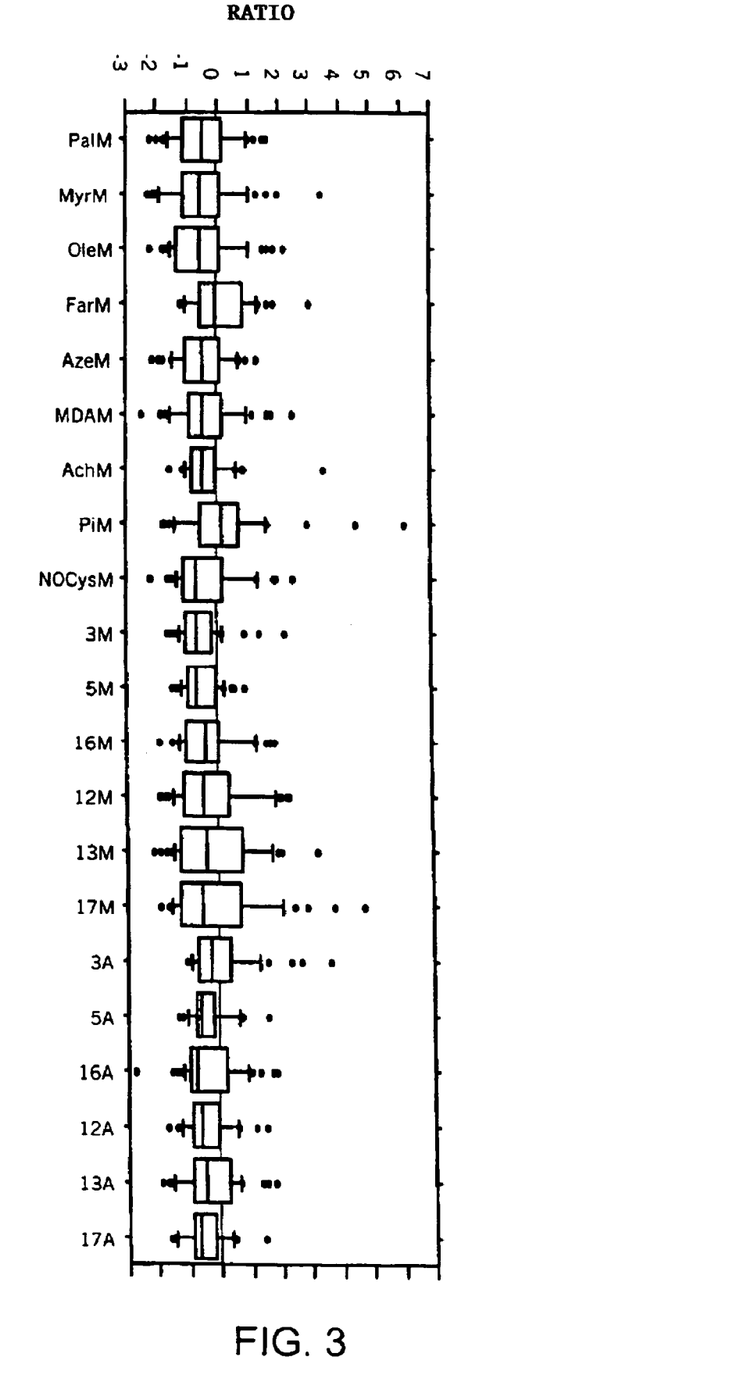
FIG. 3 is a box-plot representation of the results obtained from the quantification of immune complexes detected with 21 antigens tested in the serum from patients having class 2 of ALS compared with that of controls.
Figure 4:
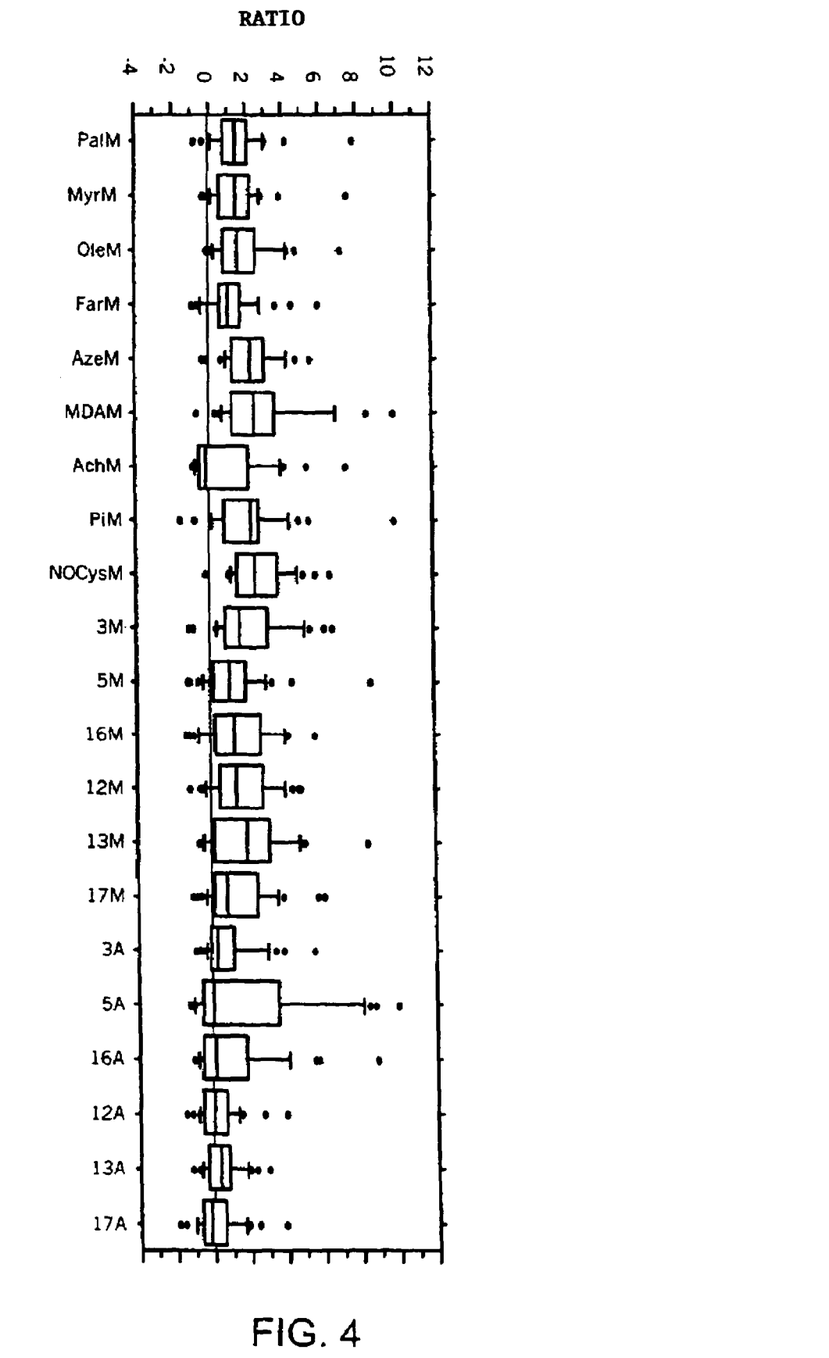
FIG. 4 is a box-plot representation of the results obtained from the quantification of immune complexes detected with 21 antigens tested in the serum from patients having class 3 of ALS compared with that of controls.

FIGS. 2 to 4 demonstrate the 3 classes of ALS:

Class 1, which is constituted by 39% of the sera tested (118 in total), is characterised by high values for the following antigens: FarCys, Ig3, Ig5, Ig16, Ig12, Ig13 and to a lesser degree Ig17 (for all these Ig, the antibodies detected are of the A-isotype)-cf. FIG. 2

Class 2, which is constituted by 34% of the sera tested, is characterised by low values for the whole of the 21 antigens (with medians<0 for 19 of them). Only FarCys and Pl attain the same level as the controls—cf. FIG. 3

Class 3, which is constituted by 27% of the sera tested, is characterised by high values, above all for the following labels: Ole, Aze, MDA, PI, NOCys, Ig3, Ig16, Ig12, Ig13, Ig17 (for all these Igs, the antibodies detected are of the M-isotype) and to a lesser degree Ig5 (for this Ig, the antibody detected is of the A-isotype)—cf. FIG. 4.

These biological profiles are to be attached to various progressive types of the ALS.

Moreover, 80% of the patients tested remain in the same group of origin during the clinical progression of their disease.

EXAMPLE 3

Quantification of the Circulating Antibodies in RA

In RA (all stages and progressions together), the significant antibodies are the antibodies which are directed against the fatty acids, azelaic acid, farnesyl-cysteine, malondialdehyde, phosphatidylinositol, NO-cysteine, NO-phenylalanine and the immunoglobulins Ig3 (A-isotype and M-isotype antibodies), Ig5 (A-isotype and M-isotype antibodies), Ig12 (A-isotype and M-isotype antibodies), Ig13 (M-isotype antibodies), Ig17 (M-isotype antibodies) and Ig19 (A-isotype antibodies), as Table 3 shows below:

TABLE 3

| Conjugate | n CON | n RA | p |
|---|---|---|---|
| Pal | 238 | 251 | <0.0001 |
| Myr | 234 | 251 | <0.0001 |
| Ole | 226 | 251 | <0.0001 |
| FarCys | 235 | 250 | 0.0005 |
| Aze | 232 | 251 | <0.0001 |
| MDA | 206 | 239 | <0.0001 |
| Ach | 229 | 251 | 0.9593 |
| PI | 209 | 251 | <0.0001 |
| NOCys | 234 | 251 | <0.0001 |
| NOTyr | 135 | 86 | 0.1471 |
| NO2Tyr | 126 | 98 | 0.7411 |
| NOTrp | 148 | 88 | 0.2906 |
| NOMet | 101 | 84 | 0.2822 |

TABLE 3-continued

| Conjugate | n CON | n RA | p |
|---|---|---|---|
| NOHis | 147 | 100 | 0.6778 |
| NOPhe | 116 | 86 | 0.0376 |
| NOAsn | 101 | 86 | 0.7968 |
| NOArg | 81 | 86 | 0.8052 |
| NOBSA | 135 | 100 | NS |
| NOCr | 46 | 77 | 0.2909 |
| Ig3* | 219 | 248 | <0.0001 |
| Ig5* | 222 | 251 | 0.0002 |
| Ig16* | 218 | 251 | 0.0772 |
| Ig12* | 221 | 251 | <0.0001 |
| Ig13* | 221 | 251 | 0.0003 |
| Ig17* | 222 | 251 | 0.0005 |
| Ig19* | 95 | 133 | 0.8907 |
| Ig3** | 226 | 248 | <0.0001 |
| Ig5** | 222 | 251 | 0.0009 |
| Ig16** | 225 | 251 | 0.2308 |
| Ig12** | 223 | 251 | 0.0140 |
| Ig13** | 220 | 251 | 0.0967 |
| Ig17** | 222 | 251 | 0.2993 |
| Ig19** | 97 | 133 | 0.0363 |

*M-isotype antibody
**A-isotype antibody

It thus appears that the titres of circulating M-isotype antibodies are an aid to the supervision of subjects ill with RA.

BIBLIOGRAPHIC REFERENCES

AMARA A., CHAUGIER C. and GEFFARD M. Autoantibodies directed against conjugated fatty acids in sera of HIV-1 infected patients. AIDS, (1994 a) 8, 711–713.

AMARA A., CHAUGIER C., RAGNAUD J.-M. and GEFFARD M. Circulating autoantibodies directed against conjugated fatty acids in sera of HIV-1 infected patients. Clinical and Experimental Immunology, (1994 b) 96, 379–383.

AMARA A., CONSTANS J., CHAUGIER C., SEBBAN A., DUBOURG L., PEUCHANT E., PELLEGRIN J. L., LENG B., CONRI C. and GEFFARD M. Autoantibodies to malondialdehyde-modified epitope in connective tissue diseases and vasculitides. Clinical and Exp. Immunol., (1995) 101, 1–6.

BOULLERNE A., PETRY K. G., MEYNARD M. and GEFFARD M. Indirect evidence for NO involvement in multiple sclerosis by characterization of circulating antibodies directed against conjugated S-nitrosocysteine. J. of Neuroimmunol., (1995) 60, 117–124.

BOULLERNE A. I., PETRY K. G. and GEFFARD M. Circulating antibodies directed against conjugated fatty acids in sera of patients with multiple sclerosis. J. of Neuroimmunol., (1996) 65, 75–81.

BROCHET B., FAIDERBE S., AUDHUY S., GOSSET I., GEFFARD M. and ORGOGOZO J. M. Antibodies against phosphatidylinositol in multiple sclerosis. Current Concepts in Multiple Sclerosis—proceedings of the 6th congress of the ECTRIMS. (Wiethölter M., Dichgans J.). MERTIN J., Eds Excerpta Medica, Amsterdam, (1991) 97–102.

CONSTANS J., CONRI C., PELLEGRIN J. L., SERGEANT C., SIMONOFF M., PEUCHANT E., DUBOURG L., THOMAS M. J., PELLEGRIN I., BROSSARD G., BARBEAU P., AMARA A., GEFFARD M., CLERC M., FLEURY H. and LENG B. Stress oxydatif and infection à VIH: un concept à préciser and une voie thérapeutique à explorer («Oxidative stress and infection with HIV: a concept to be specified and a therapeutic route to be explored»). Annales de Médecine Interne, (1995) 146, 514–520.

DAVERAT P., GEFFARD M. and ORGOGOZO J. M. Identification and characterization of anti-conjugated azelaic acid antibodies in multiple sclerosis. J. of Neuroimmunology, (1989), 22, 129–134.

FAIDERBE S., CHAGNAUD J. L., WAFFLART J. and GEFFARD M. Autoanticorps dirigés contre un phospholipide membranaire dans les sérums de malades porteurs de tumeurs malignes. («Auto-antibodies directed against a membrane phospholipid in the sera of ill subjects having malignant tumours»). CRAS, (1990) 310, 49–52.

GEFFARD M., BODET D., CLAUDEPIERRE P., METZGER J. M. and SIBILIA J. Anticorps sériques circulants dirigés contre des antigènes modifiés par le NO dans les affections neurologiques and rhumatismales. («Circulating serum antibodies directed against antigens modified by NO in neurological and rheumatic disease»), Immunoanal. Biol. Spec., (1998) 13, 209–217.

MANETA-PEYRET L., DAVERAT P., GEFFARD M., CASSGANE C. and ORGOGOZO J. M. Natural seric anti-fatty acid antibodies in multiple sclerosis. Neurosc. Letters, (1987) 80, 235–239.

SOUAN M. L., GEFFARD M., LEBRUN-GRANDIE P. and ORGOGOZO J. M. Detection of anti-acetylcholine antibodies in myasthenic patients. Neurosc. Letters. (1986) 64, 23–28.

The invention claimed is:

1. A method of detecting antibodies which are associated with the occurrence or the progression of Multiple Sclerosis in a biological fluid, which comprises the following steps:
   placing said fluid in contact with each one of the following antigens: Pl, Ach, Aze, NO-Cys, NO-Tyr, NO-Trp, NO2-Tyr, NO-Asn, NO-Met, Ig5, Ig12, Ig13, Ig16, Ig17 and Ig19,
   wherein Pl, Ach, Aze, NO-Cys, NO-Tyr, NO-Trp, NO2-Tyr, NO-Asn, NO-Met are non-bacterial antigens and wherein Ig5, Ig12, Ig13, Ig16, Ig17 and Ig19 are bacterial antigens, and
   revealing the complexes which are formed between said antigens and the corresponding antibodies,
   wherein said antibodies are of the A-isotype for bacterial antigens Ig5, Ig12, Ig13, Ig16 and Ig19, and of the M-isotype for bacterial antigens Ig12 and Ig17.

2. The method according to claim 1, in which the non-bacterial antigens other than NO-BSA are coupled to a carrier molecule.

3. The method according to claim 2, wherein said carrier molecule is bovine serum albumin.

4. The method according to claim 1, in which the complex which is formed is revealed with the aid of an anti-human immunoglobin antibody of the M-isotype or of the A-isotype, said antibody being labelled.

5. The method according to claim 4, wherein said antibody is labeled by an enzyme.

6. The method according to claim 1, in which the enzyme is peroxidase.

7. The method according to claim 1, which is carried out with the aid of a solid support.

8. The method according to claim 7, wherein said solid support is a microtitration plate.

9. A method of detecting antibodies which are associated with the occurrence or the progression of Amyotrophical Lateral Sclerosis in a biological fluid, which comprises the following steps:

placing said fluid in contact with each one of the following antigens:

Ole, Pl, MDA, Aze, NO-Cys, FarCys, Ig3, Ig5, Ig12, Ig13, Ig16 and Ig17, wherein Ole, Pl, MDA, Aze, NO-Cys, FarCys are non-bacterial antigens and wherein Ig3, Ig5, Ig12, Ig13, Ig16 and Ig17 are bacterial antigens, and revealing the complexes which are formed between said antigens and the corresponding antibodies, wherein said antibodies are of the A-isotype for bacterial antigens Ig3, Ig5, Ig12, Ig13, Ig16 and Ig17, and of the M-isotype for bacterial antigens Ig3, Ig12, Ig13, Ig16 and Ig17.

10. The method according to claim 9, in which the non-bacterial antigens other than NO-BSA are coupled to a carrier molecule.

11. The method according to claim 9, in which the complex which is formed is revealed with the aid of an anti-human immunoglobin antibody of the M-isotype or of the A-isotype, said antibody being labelled.

12. The method according to claim 9, in which the enzyme is peroxidase.

13. The method according to claim 9, which is carried out with the aid of a solid support.

14. A method of detecting antibodies which are associated with the occurrence or the progression of Rheumatoid Arthritis in a biological fluid, which comprises the following steps:

placing said fluid in contact with each one of the following antigens:

Pal, Ole, Myr, Pl, MDA, FarCys, Aze, NO-Cys, NO-Phe, Ig3, Ig5, Ig12, Ig13, Ig17 and Ig19, wherein Pal, Ole, Myr. Pl, MDA, FarCys, Aze, NO-Cys, NO-Phe are non-bacterial antigens and wherein Ig3, Ig5, Ig12, Ig13, Ig17 and Ig19 are bacterial antigens, and revealing the complexes which are formed between said antigens and the corresponding antibodies, wherein said antibodies are of the A-isotype for bacterial antigens Ig3, Ig5, Ig12 and Ig19, and of the M-isotype for bacterial antigens Ig3, Ig5, Ig12, Ig13 and Ig17.

15. The method according to claim 14, in which the non-bacterial antigens other than NO-BSA are coupled to a carrier molecule.

16. The method according to claim 14, in which the complex which is formed is revealed with the aid of an anti-human immunoglobin antibody of the M-isotype or of the A-isotype, said antibody being labelled.

17. The method according to claim 14, in which the enzyme is peroxidase.

18. The method according to claim 14, which is carried out with the aid of a solid support.

19. A method for diagnosing the occurrence or the progression of Multiple Sclerosis in a subject, said method comprising:

(a) placing a biological fluid of said subject in contact with each one of the antigens as defined in claim 1;

(b) detecting circulating antibodies by revealing the complexes which are formed between the antigens and the corresponding antibodies as defined in claim 1; and (c) expressing and comparing the results of the detected circulating antibodies with respect to a control population.

20. A method for diagnosing the occurrence or the progression of Amyotrophical Lateral Sclerosis in a subject, said method comprising:

(a) placing a biological fluid of said subject in contact with each one of the antigens as defined in claim 9;

(b) detecting circulating antibodies by revealing the complexes which are formed between the antigens and the corresponding antibodies as defined in claim 9; and (c) expressing and comparing the results of the detected circulating antibodies with respect to a control population.

21. A method for diagnosing the occurrence or the progression of Rheumatoid Arthritis in a subject, said method comprising:

(a) placing a biological fluid of said subject in contact with each one of the antigens as defined in claim 14;

(b) detecting circulating antibodies by revealing the complexes which are formed between the antigens and the corresponding antibodies as defined in claim 14; and (c) expressing and comparing the results of the detected circulating antibodies with respect to a control population.

22. A kit for the implementation of the method according to claim 1, which comprises each one of the following antigens: Pl, Ach, Aze, NO-Cys, NO-Tyr, NO-Trp, NO2-Tyr, NO-Asn, NO-Met, Ig5, Ig12, Ig13, Ig16, Ig17 and Ig19.

23. The kit according to claim 22, in which the non-bacterial antigens other than NO-BSA are coupled to a carrier molecule.

24. The kit according to claim 23, wherein said carrier molecule is bovine serum albumin.

25. The kit according to claim 22, which also comprises at least one antibody selected from the group consisting of anti-human immunoglobin antibodies of the M-isotype and anti-human immunoglobin antibodies of the A-isotype.

26. A kit for the implementation of the method according to claim 9, which comprises each one of the following antigens: Ole, Pl, MDA, Aze, NO-Cys, FarCys, Ig3, Ig5, Ig12, Ig13, Ig16 and Ig17.

27. A kit for the implementation of the method according to claim 14, which comprises each one of the following antigens: Pal, Ole, Myr , Pl, MDA, FarCys, Aze, NO-Cys, NO-Phe, Ig3, Ig5, Ig12, Ig13, Ig17 and Ig19.

* * * * *